United States Patent [19]

Oude Alink

[11] Patent Number: 4,564,707
[45] Date of Patent: Jan. 14, 1986

[54] LINEAR N,N'-TETRASUBSTITUTED DIAMINES AND PROCESS FOR THEIR PREPARATION

[75] Inventor: Bernardus A. Oude Alink, St. Louis, Mo.

[73] Assignee: Petrolite Corporation, St. Louis, Mo.

[21] Appl. No.: 245,469

[22] Filed: Mar. 19, 1981

Related U.S. Application Data

[62] Division of Ser. No. 873,322, Jan. 30, 1978, Pat. No. 4,281,126.

[51] Int. Cl.$^4$ ............................................. C07C 85/20
[52] U.S. Cl. .................................. 564/413; 544/242; 544/335; 564/367; 564/372; 564/511
[58] Field of Search ............... 544/242; 564/367, 372, 564/413, 511

[56] References Cited

U.S. PATENT DOCUMENTS

| | | | |
|---|---|---|---|
| 2,058,615 | 10/1936 | Morton | 564/336 X |
| 2,486,648 | 11/1949 | Hanry | 564/487 |
| 2,535,747 | 12/1950 | Morey | 544/242 |
| 2,652,430 | 9/1953 | Finch et al. | 564/470 |
| 3,396,150 | 8/1968 | Dickinson et al. | 564/511 X |
| 3,787,416 | 1/1974 | Cyba | 544/335 |
| 3,904,625 | 9/1975 | Oude Alink | 544/242 |
| 4,059,548 | 11/1977 | Gaudette et al. | 544/242 |
| 4,104,249 | 8/1978 | Oude Alink et al. | |
| 4,281,126 | 7/1981 | Oude Alink | 544/242 |

OTHER PUBLICATIONS

Bergmann et al., "Jour. Org. Chem.", vol. 13, pp. 353–356 (1947).
Popel et al., "Jour. Prakt. Chem.", vol. 38, 5–6, pp. 335–347 (1968).
Brown, "Heterocyclic Compounds", The Pyrimidines, and Supplement 1, pp. 452–453 (1962) and p. 353 (1970).
The Merck Index, 9th Ed., p. ONR-28 (1976).
Bradbury et al., "Jour. Chem. Soc. London", pp. 1394–1399 (1947).
Evans, "Aust. Jour. Chem.", vol. 20, pp. 1643–1647, and 1656–1657 (1567).

Primary Examiner—Robert V. Hines
Attorney, Agent, or Firm—Sidney B. Ring; Leon J. Bercovitz

[57] ABSTRACT

This invention relates to the following compounds:

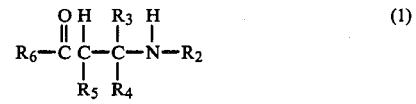

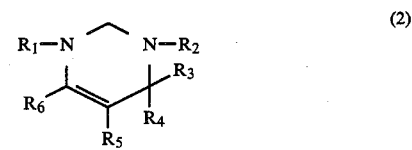

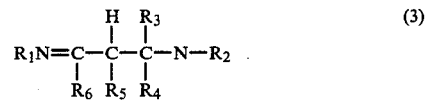

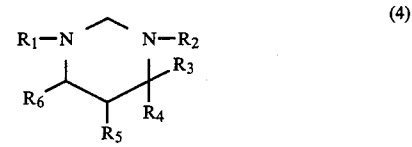

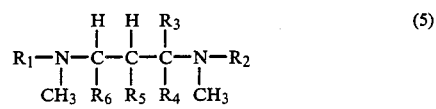

Process for their preparation and uses thereof, where $R_1$ and $R_2$ are substituted groups, and $R_6$, $R_5$, $R_4$ and $R_3$ are hydrogen or substituted groups.

10 Claims, No Drawings

LINEAR N,N'-TETRASUBSTITUTED DIAMINES AND PROCESS FOR THEIR PREPARATION

This is a division of application Ser. No. 873,322, filed Jan. 30, 1978 and now U.S. Pat. No. 4,281,126.

This invention relates to the preparation of 1,2,3,4-tetrahydropyrimides (THP) by reacting an $\alpha,\beta$-unsaturated carbonyl compound with an amine, for example, as follows:

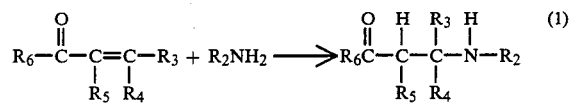

(2) Then reacting the product of (1) with an amine and formaldehyde, for example, as follows:

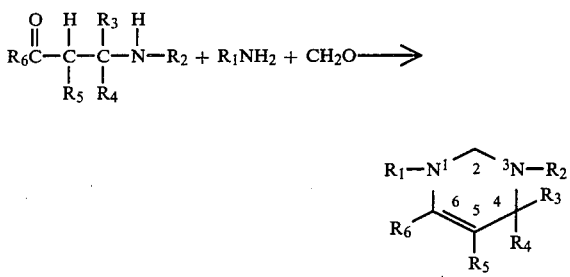

(2a) Note: the reaction can be facilitated by employing a dehydration agent, for example, as follows:

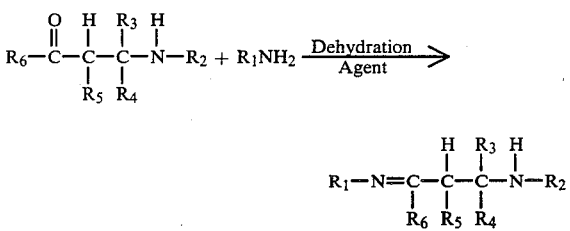

which can then be cyclized with $CH_2O$ to form THP.
(3) The THP formed in (2) or (2a) can be reduced to HHP according to the equation

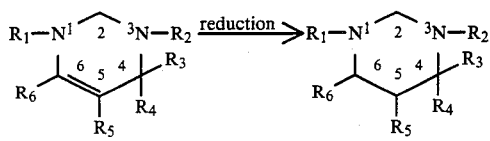

(4) The HHP of (3) can be converted to a linear N,N'-tetrasubstituted diamine, for example, as follows

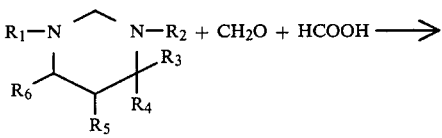

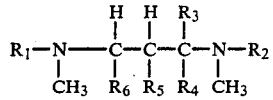

$R_1$ and $R_2$ are substituted groups such as alkyl, alkenyl, aryl, cycloalkyl, aralkyl, heterocyclic which groups may also contain functional groups such as hydroxy, amino, etc., groups and $R_3$, $R_4$, $R_5$ and $R_6$ are hydrogen, alkyl, alkenyl, aryl, aralkyl, cycloalkyl and heterocyclic. $R_1$ and $R_2$ may be the same or different.

In general, all steps are carried out under any suitable conditions capable of effecting reaction. In general, the reactions are carried out at temperature of from about 0°–150° C. such as from about 0°–100° C., but in practice from about 10°–50° C. The reactions may be carried out with or without a solvent. Reaction time is generally from about 0.5 to 24 hrs. such as from about 1 to 10 hrs. but practically from about 1 to 8 hrs.

Any suitable dehydrating agent can be employed in reaction 2a, such as for example, $CaCl_2$, $K_2CO_3$, $MgSO_4$, $CaSO_4$, molecular sieves, etc.

The reduction of the THP can be effected by any suitable means for example by employing catalytic hydrogenation, aluminum isopropoxide, formic acid, sodium in ethanol, sodium hydrosulfate, trimethylammonium formate, zinc amalgam, etc.

The following examples are presented for purposes of illustration and not of limitation.

EXAMPLE 1

1,3,4,4,6-Pentamethyl 1,2,3,4-Tetrahydropyrimidine

A sample of 196 grams of mesityl oxide was cooled in an ice bath. Over a 30 minute period a sample of 310 grams of 40% aqueous methylamine solution was added at such a rate that the reaction temperature did not exceed 28° C. After the addition was completed, stirring was continued for 10 minutes. To the cooled reaction mixture was added over a 15 minute period, a sample of 162 grams of a 37% formaldehyde solution while maintaining a reaction temperature below 29° C. To the homogeneous solution was added 20 grams of sodium hydroxide pellets. The organic layer which separated was removed and the aqueous layer extracted with ether. The ethereal solution was combined with the organic phase and evaporated under diminished pressure. Distillation yielded a fraction of 218 grams $b_{20}$ 65°–85° C., which was redistilled to yield a fraction $b_{20}$ 69°–75° C.; identified as 1,3,4,4,6-Pentamethyl 1,2,3,4-tetrahydropyrimidine, Infrared spectrum 6.1$\mu$, N—C=C— group; $C^{13}$ n.m.r. spectrum, solvent $CDCl_3$, $\delta$ in ppm.

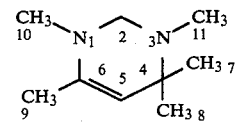

69.6(2); 53.6(4); 108.4(5); 138.4(6); 26.3(7); 26.3(8); 19.1(9); 36.6*(10); 35.3(11)*
*assignments may be reversed Anal: Calculated for $C_9H_{18}N_2$: N, 18.2. Found: N, 18.4.

EXAMPLE 2

1,3,4,4,6-Pentamethyl hexahydropyrimidine

A sample of 55.2 grams of 1,3,4,4,6-pentamethyl 1,2,3,4-tetrahydropyrimidine prepared as described in example 1, was dissolved in 128 grams of absolute ethanol. To the stirred mixture was added 8 grams of sodium tetrahydridoborate, (NaBH$_4$), in three portions over a 1½ hours period. The mixture was stirred for 18 more hours and the solvent removed under diminished pressure. The remaining product was treated with water containing a small amount of ammonium chloride and extracted with ether. The ethereal solution was evaporated under diminished pressure and the remaining product distilled under diminished pressure, to yield 36.8 grams, b$_{20}$ 73°–76° C., of a product identified as 1,3,4,4,6-pentamethyl hexahydropyrimidine, C$^{13}$ n.m.r. spectrum, solvent CDCl$_3$, δ in ppm.

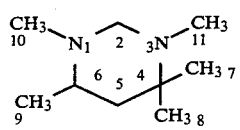

74.2(2); 52.5(4); 46.0(5); 54.1(6); 29.8(7); 20.0(8); 15.5(9); 38.6(10); 34.7(11).

Anal. Calculated for C$_9$H$_{20}$N$_2$: N, 18.0. Found: N, 17.9

EXAMPLE 3

N,N'-Tetramethyl 2,4-diamino 2-methylpentane

A sample of 3.1 grams of 1,3,4,4,6-pentamethyl hexahydropyrimidine prepared as described in example 2, 2 grams of 37% aqueous formaldehyde, and 5.1 grams of 97% formic acid was mixed and refluxed for 19 hours. The mixture was cooled and 5 grams of conc. HCl in 5 grams of water was added. The mixture was refluxed for 1 hour, cooled to ambient temperature and basified with aqueous sodium hydroxide. The resulting mixture was extracted with ether, and the ethereal solution, after drying, evaporated under diminished pressure to yield 3 grams of N,N'-tetramethyl 2,4-diamine 2-methyl pentane; N.m.r. solvent CDCl$_3$, δ in ppm, 2.73 m, (1H); 2.20, s, (6H); 2.16, s, (6H); 1.46, m, (2H); 1.00 s, (6H); and 0.98 d, (3H). C$^{13}$ n.m.r., solvent CDCl$_3$, δ in ppm;

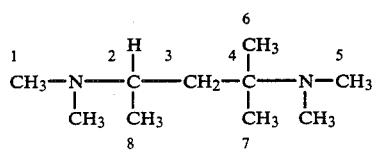

40.0(1); 54.8(2); 43.1(3); 55.6(4); 38.5(5); 22.9(6)\*; 23.4(7)\*; 14.3(8).

\*assignments are not unambiguous

EXAMPLE 4

1,3-Dibutyl 4,4,6-trimethyl 1,2,3,4-tetrahydropyrimidine

A mixture of 49 grams of mesityloxide and 72 grams of butylamine was stirred for 19 hours. To the mixture was added 80 cc of isopropanol and 39 cc of 37% formaldehyde solution and stirring was continued for 1 hour. Distillation of the product under diminished pressure yielded 45 grams, b$_{0.2}$ 112°–118° C., of 1,3-dibutyl 4,4,6-trimethyl 1,2,3,4-tetrahydropyrimidine. Infrared spectrum, 6.05μ, N—C=C— moiety; C$^{13}$ n.m.r., solvent CDCl$_3$.

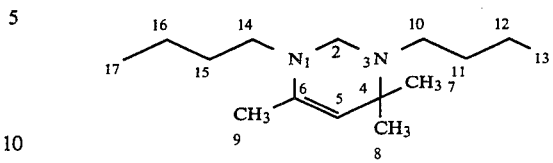

63.2(2); 54.1(4); 111.4(5); 138.0(6); 25.4(7,8); 19.3(9); 49.2(10); 31.4(11); 20.7(12,16); 14.0(13,17); 45.7(14); 30.9(15)

EXAMPLE 5

1,3-Diallyl 4,4,6-trimethyl 1,2,3,4-tetrahydropyrimidine

A mixture of 30.2 grams of allylamine and 25.2 grams of mesityloxide was stirred for 17 hours. A mixture of 40 cc isopropanol and 20 cc of 37% formaldehyde was added. Stirring was continued for 1½ hours. The solvent was removed under diminished pressure and the product distilled. The fraction, b$_{0.2}$, 70°–74° C., was collected as 39 grams of 1,3-diallyl 4,4,6-trimethyl 1,2,3,4-tetrahydropyrimidine, C$^{13}$ n.m.r., solvent CDCl$_3$, δ in ppm;

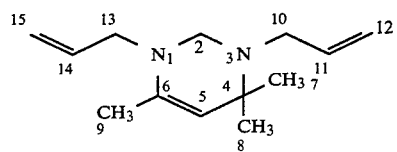

62.5(2); 54.2(4); 111.0(5); 137.5(6); 25.8(7,8); 19.2(9); 45.2(10); 136.1(11,14); 116.2(12,15); 49.6(13)

EXAMPLE 6

1,3-Diallyl 4,4,6-trimethyl hexahydropyrimidine

To a mixture of 45 grams of 1,3-diallyl 4,4,6-trimethyl 1,2,3,4-tetrahydropyrimidine, prepared as described in example 5 and 101 grams of absolute ethanol, was added, over a 1 hour period 5.1 grams of sodium tetrahydridoborate. The reaction mixture was stirred for 18 hours and the ethanol removed under diminished pressure. The resulting product was partitioned between water and ether. The ethereal solution was evaporated under diminished pressure to yield 39 grams of product. Distillation of a 36.5 grams of a sample yielded 22 grams of b$_{0.1}$, 74°–78° C. which was identified as 1,3-diallyl 4,4,6-trimethyl hexahydropyrimidine.

Anal: Calc.ed for C$_{13}$H$_{24}$N$_2$: N, 13.46. Found: N, 13.56.

EXAMPLE 7

1-butyl 3,4,4,6-tetramethyl 1,2,3,4-tetrahydropyrimidine

A sample of 49 grams (0.5M) of mesityloxide was cooled in an ice-water bath. To the mesityloxide was added over a 10 minute period 40 grams of a 40% aqueous methylamine solution while maintaining a reaction temperature of lower than 30° C. After the addition was completed, stirring was continued for 15 minutes and 36.5 grams (0.5M) of butylamine was added all at once. The mixture was cooled and over a 5 minute period 39 cc of a 37% solution of formaldehyde was added. Stirring was continued for ½ hour. The organic layer which separated was removed, and the aqueous phase extracted with ether. The ethereal solution was combined with the organic layer and evaporated under diminished pressure to yield 90 grams of crude 1-butyl 3,4,4,6-tetramethyl 1,2,3,4-tetrahydropyrimidine. A sample of 46.8 grams was distilled under diminished pressure and the fraction, 29 grams of $b_{0.5}$ 75°–80° C., was collected. $C^{13}$ n.m.r. spectrum, solvent $CDCl_3$, ref. T.M.S.:

67.0(2); 53.8(4); 107.7(5); 137.7(6); 26.5(7,8); 19.4(9); 35.3(10); 49.0(11); 31.2(12); 20.4(13); 14.0(14).

Anal. Calc.ed for $C_{12}H_{24}N_2$: N, 14.29. Found: N, 13.2.

EXAMPLE 8

1-Butyl 3,4,4,6-tetramethyl hexahydropyrimidine

To a mixture of 40 grams of 1-butyl 3,4,4,6-tetramethyl 1,2,3,4-tetrahydropyrimidine prepared as described in example 7, and 177 grams of absolute ethanol was added over a ½ hour period 4.7 grams of sodium hydridoborate. The reaction mixture was stirred for 18 hours and the ethanol evaporated under diminished pressure. To the resulting product was added water and stirring was continued for 24 hours. The organic layer was separated, dissolved in ether, and the ethereal solution washed with diminished pressure to yield 38.5 grams of 1-butyl 3,4,4,6-tetramethyl hexahydropyrimidine. $C^{13}$ n.m.r., solvent $CDCl_3$; ref. T.M.S.;

71.2(2); 52.4(4); 46.4(5); 52.1(6); 29.7(7); 20.4(8); 15.3(9); 34.7(10); 49.6(11); 29.5(12); 20.9(13); 14.0(14).

As described above the following substituted 1,2,3,4-tetrahydropyrimidines of the general structure:

were prepared, and are listed in Table I.

TABLE I

| Example No. | $R_1$ | $R_2$ | $R_3$ | $R_4$ | $R_5$ | $R_6$ |
|---|---|---|---|---|---|---|
| 9 | $CH_3$–$(CH_2)_5$ | $CH_3$–$(CH_2)_5$ | $CH_3$ | $CH_3$ | H | $CH_3$ |
| 10 | $CH_3$ | $CH_3$ | $CH_3$ | $CH_3$ | –$(CH_2)_4$– | |
| 11 | $CH_3$—CH=$CH_2$— | $CH_3$ | $CH_3$ | $CH_3$ | H | $CH_3$ |
| 12 | HO—$CH_2$—$CH_2$— | $CH_3$ | $CH_3$ | $CH_3$ | H | $CH_3$ |
| 13 | $CH_3$ | $CH_3$ | –$(CH_2)_5$ | –$(CH_2)_4$ | | |
| 14 | $CH_3CH_2$ | $CH_3$—$CH_2$ | $CH_3$ | $CH_3$ | H | $CH_3$ |
| 15 | Phenyl-$CH_2$— | $CH_3$ | $CH_3$ | $CH_3$ | H | $CH_3$ |
| 16 | $(CH_3)_2$—N—$CH_2$—$CH_2$ | $CH_3$ | $CH_3$ | $CH_3$ | H | $CH_3$ |

The compositions of this invention have a wide variety of uses, including their use as corrosion inhibitors, biocides, scale inhibitors, fuel additives -etc.

I claim:

1. A process which comprises reacting a compound of the formula where $R_1$ and $R_2$ are alkyl, alkenyl, aryl, cycloalkyl, arakyl or heterocyclic groups or amino substituted derivatives thereof and $R_6$, $R_5$, $R_4$ and $R_3$ are hydrogen or substituted groups with formaldehyde and formic acid.

2. The process of claim 1 where $R_1$, $R_2$, $R_3$, $R_4$ and $R_6$ are hydrocarbon groups and $R_5$ is hydrogen.

3. The process of claim 2 where $R_1$, $R_2$, $R_3$, $R_4$ and $R_6$ are methyl and $R_5$ is hydrogen.

4. The process of claim 1 in which the reaction takes place at a temperature of from about 0° C. to about 150° C.

5. The process of claim 4 where the reaction takes place at reflux temperature.

6. The product obtained by the process of claim 1.
7. The product obtained by the process of claim 2.
8. The product obtained by the process of claim 3.
9. The product obtained by the process of claim 4.
10. The product obtained by the process of claim 5.

* * * * *